(12) United States Patent
Duarte

(10) Patent No.: US 7,039,450 B2
(45) Date of Patent: May 2, 2006

(54) TELESCOPING CATHETER

(75) Inventor: Maria J. Duarte, Chino, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 231 days.

(21) Appl. No.: 10/665,303

(22) Filed: Sep. 18, 2003

(65) Prior Publication Data

US 2004/0097819 A1 May 20, 2004

Related U.S. Application Data

(60) Provisional application No. 60/426,834, filed on Nov. 15, 2002.

(51) Int. Cl.
*A61B 5/42* (2006.01)
(52) U.S. Cl. ..................... 600/374; 600/381
(58) Field of Classification Search ............... 600/374, 600/381; 606/41; 607/122
See application file for complete search history.

(56) References Cited

U.S. PATENT DOCUMENTS

| | | | |
|---|---|---|---|
| 5,313,943 A * | 5/1994 | Houser et al. ............... | 600/374 |
| 5,848,986 A | 12/1998 | Lundquist et al. | |
| 5,881,727 A * | 3/1999 | Edwards ..................... | 600/374 |
| 5,897,529 A * | 4/1999 | Ponzi ........................ | 604/95.04 |
| 6,088,610 A * | 7/2000 | Littmann et al. ............ | 600/381 |
| 6,138,043 A | 10/2000 | Avitall | |
| 6,198,974 B1 * | 3/2001 | Webster, Jr. ................ | 607/122 |
| 6,238,389 B1 | 5/2001 | Paddock et al. | |
| 2002/0161422 A1 | 10/2002 | Swanson et al. | |
| 2002/0177765 A1 * | 11/2002 | Bowe et al. ................ | 600/374 |
| 2003/0004509 A1 * | 1/2003 | Falwell et al. .............. | 606/41 |

FOREIGN PATENT DOCUMENTS

WO     WO 95/10225     4/1995

* cited by examiner

*Primary Examiner*—Lee S. Cohen
(74) *Attorney, Agent, or Firm*—Christie, Parker & Hale, LLP

(57) ABSTRACT

A catheter that is particularly useful for mapping electrical activity in the heart of a patient is provided. The catheter comprises an elongated catheter body having a lumen extending longitudinally therethrough. A control handle is attached to the proximal end of the catheter body and includes first and second members that are moveable relative to each other. The second member is attached to the catheter body. An inner member is slidably mounted in the lumen of the catheter body. The inner member comprises an elongated stiffening member that is surrounded by and connected to a non-conductive covering having a free distal end on which is mounted one or more electrodes. The proximal end of the inner member is attached to the first member of the control handle. Longitudinal movement of the first member relative to the second member results in longitudinal movement of the inner member relative to the catheter body to cause the inner member to extend out of and retract into the catheter body.

12 Claims, 3 Drawing Sheets

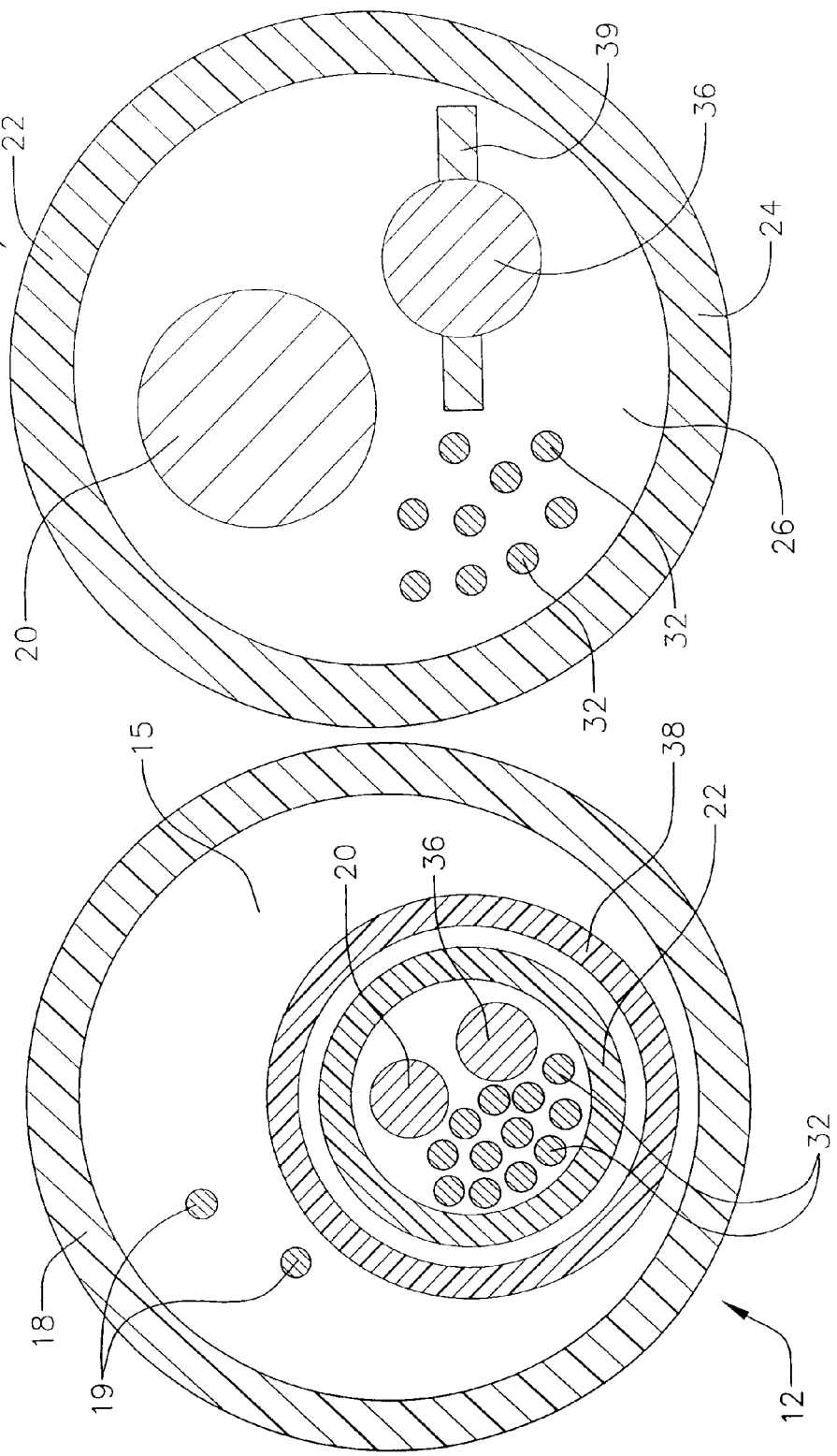

TELESCOPING CATHETER

CROSS-REFERENCE TO RELATED APPLICATION(S)

This application claims the benefit of U.S. Provisional Patent Application No. 60/426,834, filed Nov. 15, 2002, the entire disclosure of which is incorporated herein by reference.

BACKGROUND

Electrophysiology catheters are commonly used for mapping electrical activity in a heart. By mapping the electrical activity in the heart, one can detect ectopic sites of electrical activation or other electrical activation pathways that contribute to heart malfunctions. This type of information may then allow a cardiologist to intervene and destroy the malfunctioning heart tissues. Such destruction of heart tissue is referred to as ablation, which is a rapidly growing field within electrophysiology and obviates the need for maximally invasive open heart surgery.

Such electrophysiology mapping catheters typically have an elongated flexible body with a distal end that carries one or more electrodes that are used to map or collect electrical information about the electrical activity in the heart. The distal end can be deflectable to assist the user in properly positioning the catheter for mapping in a desired location. Typically, such catheters can be deflected to form a single curve. It is desirable to have a catheter that can be deflective to form a variety of curves to thereby map an entire region where a single curve may not be sufficient.

SUMMARY OF THE INVENTION

The present invention is directed to an improved catheter that is particularly useful for mapping electrical activity in a heart of a patient and that allows the user to vary curve preferences as well as the number of electrodes to be used to map a particular area of tissue.

In one embodiment, the invention is directed to a catheter comprising an elongated catheter body having a proximal end, a distal end and a lumen extending longitudinally therethrough. A control handle is attached to the proximal end of the catheter body. The control handle includes a first member, such as housing, that is moveable relative to a second member, such as a piston slidably mounted in the housing. The catheter body is attached to the second member.

An inner member is slidably mounted in the lumen of the catheter body. The inner member comprises an elongated stiffening member, having proximal and distal ends, that is surrounded by and connected to a non-conductive covering. The non-conductive covering has a free distal end on which is mounted one or more electrodes. The proximal end of the inner member is attached to the first member of the control handle. Longitudinal movement of the first member relative to the second member results in longitudinal movement of the inner member relative to the catheter body to cause the inner member to extend out of and retract into the catheter body.

DESCRIPTION OF THE DRAWINGS

These and other features and advantages of the present invention will be better understood by reference to the following detailed description when considered in conjunction with the accompanying drawings wherein:

FIG. 2 is an end cross-sectional view of the catheter body of the catheter of FIG. 1 taken along line 2—2.

FIG. 3 is an end cross-sectional view of the inner member of the catheter of FIG. 1 taken along line 3—3.

DETAILED DESCRIPTION OF THE INVENTION

Figure 1:
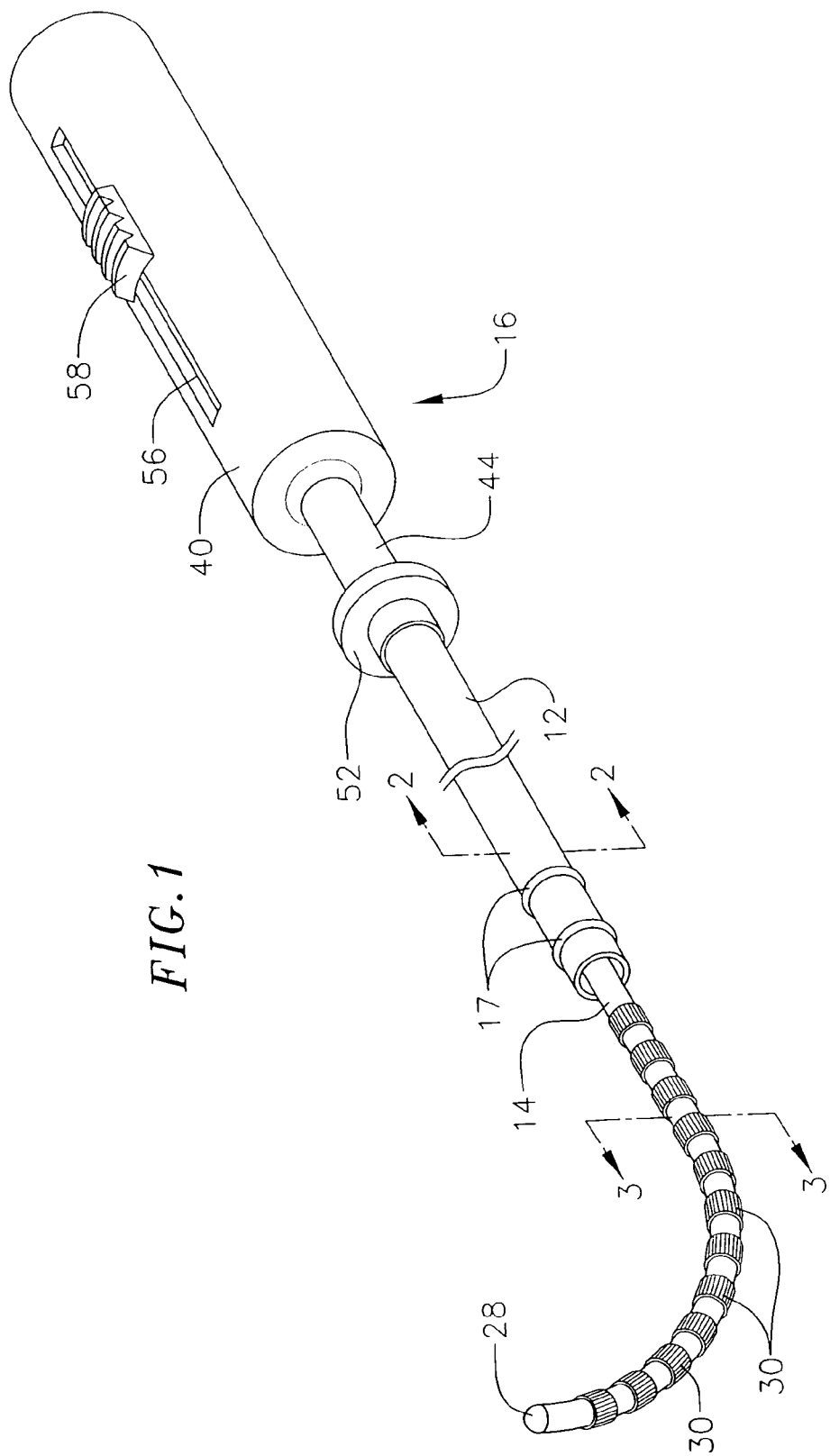
FIG. 1 is a perspective view of a catheter according to the invention.

The invention is directed to a telescoping catheter having an extendable and retractable mapping assembly at the distal end of the catheter that is deflectable. As shown in FIG. 1, the catheter comprises an elongated catheter body 12 having proximal and distal ends, an elongated telescoping inner member 14 extending through the catheter body, and a control handle 16 at the proximal end of the catheter body. The catheter body 12 comprises an elongated tubular construction having a single, axial or central lumen 15, as shown in FIG. 2, but can optionally have multiple lumens along all or part of its length if desired. The catheter body 12 is flexible, i.e., bendable, but substantially non-compressible along its length. The catheter body 12 can be of any suitable construction and made of any suitable material. A presently preferred construction of the catheter body 12 comprises an outer wall 18 made of polyurethane or PEBAX® (polyether block amide). The outer wall 18 preferably comprises an imbedded braided mesh of stainless steel or the like, as is generally known in the art, to increase torsional stiffness of the catheter body 12 so that, when the control handle 16 is rotated, the distal end of the catheter body 12 will rotate in a corresponding manner.

The length of the catheter body 12 is not critical, but preferably ranges from about 90 cm to about 120 cm, and more preferably is about 110 cm. The outer diameter of the catheter body 12 is also not critical, but is preferably no more than about 8 french, more preferably about 7 french. Likewise, the thickness of the outer wall 18 is not critical, but is preferably thin enough so that the central lumen 15 can accommodate all necessary wires and other components extending through the catheter body 12.

In the depicted embodiment, two ring electrodes 17 are mounted, preferably evenly-spaced, along the distal end of the catheter body 12. As would be recognized by one skilled in the art, the number and arrangement of the electrodes on the catheter body can vary as desired, or the electrodes can be eliminated altogether. Each ring electrode 17 is electrically connected to an electrode lead wire 19, which in turn is electrically connected to a connector 34 at the proximal end of the catheter, which is connected to an appropriate mapping or monitoring system (not shown). Each electrode lead wire 19 extends from the connector 34, through the control handle 16, and into the central lumen 15 of the catheter body 12 where it is attached to its corresponding ring electrode 17. Each lead wire 19, which includes a non-conductive coating over almost all of its length, is attached to its corresponding ring electrode 17 by any suitable method.

The inner member 14 is slidably mounted within the central lumen 15 of the catheter body 12. As best shown in FIG. 3, the inner member 14 comprises an elongated stiffening member 20 surrounded by a flexible non-conductive cover 22. The stiffening member 20 preferably comprises a superelastic material, for example a nickel-titanium alloy such as nitinol, but can comprise any other suitable material, such as stainless steel or plastic. The non-conductive cover 22 preferably comprises a biocompatible plastic tubing, such as a polyurethane or polyimide tubing. In the depicted embodiment, the non-conductive cover 22 has an outer wall 24 with a single lumen 26 extending therethrough, but could alternatively include multiple lumens. The non-conductive cover 22, and thus the inner member 14, has a free distal end, i.e., a distal end that is not connected or attached to any other part of the inner member, to the catheter body, or to any other external structure that confines movement of the distal end.

In the depicted embodiment, the distal end of the inner member 14 has an atraumatic tip comprising a plastic cap 28, preferably made of polyurethane. The plastic cap 28 is glued or otherwise fixedly attached to the distal end of the inner member 14. Other atraumatic tip designs could be used in connection with the invention, or the use of an atraumatic tip can be eliminated.

The inner member 14 carries one or more electrodes along its distal end. In the depicted embodiment, twelve ring electrodes 30 are mounted, preferably evenly-spaced, along the distal end of the non-conductive cover 22. As would be recognized by one skilled in the art, the number and arrangement of the electrodes on the inner member can vary as desired. For example, the inner member 14 could carry a tip electrode (not shown) on the distal end of the spine in place of the plastic cap 28. Each ring electrode 30 has a length preferably up to about 2 mm, more preferably from about 0.5 mm to about 1 mm. The distance between the ring electrodes 28 preferably ranges from about 1 mm to about 10 mm, more preferably from about 2 mm to about 5 mm. Preferably the inner member 14 carries from 2 to about 20 electrodes, more preferably from 3 to about 15 electrodes.

Each ring electrode 30 is electrically connected to an electrode lead wire 32, which in turn is electrically connected to the connector 34, which is connected to an appropriate mapping or monitoring system (not shown). In the depicted embodiment, the inner member electrode lead wires 32 are connected to the same connector as the catheter body electrode lead wires 19, but could also be connected to a different connector depending on the desired application. Each electrode lead wire 32 extends from the connector 34, through the control handle 16, and into the non-conductive cover 22 of the inner member 14 where it is attached to its corresponding ring electrode 30. Each lead wire 32, which includes a non-conductive coating over almost all of its length, is attached to its corresponding ring electrode 30 by any suitable method.

A preferred method for attaching a lead wire 19 or 32 to a ring electrode 17 or 30 involves first making a small hole through the outer wall of the catheter body 12 or non-conductive cover 22. Such a hole can be created, for example, by inserting a needle through the outer wall and heating the needle sufficiently to form a permanent hole. The lead wire 19 or 32 is then drawn through the hole by using a microhook or the like. The end of the lead wire 19 or 32 is then stripped of any coating and welded to the underside of the corresponding ring electrode 17 or 30, which is then slid into position over the hole and fixed in place with polyurethane glue or the like. Alternatively, each ring electrode 19 or 30 may be formed by wrapping the lead wire 17 or 32 around the catheter body 12 or non-conductive cover 22 a number of times and stripping the lead wire of its own non-conductive coating on its outwardly facing surfaces. In such an instance, the lead wire functions as a ring electrode.

The inner member 14 is moveable between a retracted position, where the entire inner member is contained within the central lumen 15 of the catheter body 12, and a fully extended position, where all of the electrodes 30 mounted on the inner member extend beyond the distal end of the catheter body. The length of the exposed portion of the inner member 14 when in the fully extended position preferably ranges from about 10 mm to about 200 mm. The inner member 14 can also be moved to one or more intermediate extended positions where the distal end of the inner member 14 extends beyond the distal end of the catheter body 12, but one or more of the electrodes 30 are still contained within the central lumen 15 of the catheter body. To affect such movement, the proximal end of the stiffening member 20 is attached to the control handle 16, as discussed in more detail below.

In the depicted embodiment, the distal end of the stiffening member 20 is attached to the distal end of the inner member 14, and indirectly to the distal end of the non-conductive cover 22, by being glued or otherwise attached to the plastic cap 28. The stiffening member 20 can be attached, directly or indirectly, to the non-conductive cover 22 in any other manner and at any other position along the length of the inner member 14. However, it is currently preferred that the stiffening member 20 be attached to the non-conductive cover 22 closer to the distal end of the inner member 14 to permit the user to have better control when extending and retracting the inner member.

In the depicted embodiment, the non-conductive cover 22 extends the full length of the catheter body 12 with its proximal end in the control handle 16. However, if desired, the non-conductive cover 22 can terminate at its proximal end at any position within the catheter body 12. The non-conductive cover 22 should be sufficiently long so that, when the inner member 14 is in its fully extended position, at least a portion of the non-conductive cover is maintained within the catheter body 12.

Within the catheter body 12, the inner member 14 extends through a sleeve 38, preferably made of plastic, such as nylon. The sleeve 38 serves as a lumen for the inner member 14 within the catheter body 12. In particular, the sleeve 38 protects the inner member 14 from interfering or getting tangled with the lead wires 19 that extend through the catheter body 12 when the inner member 14 is being extended or retracted.

Additionally, a mechanism is provided for deflecting the distal end of the inner member 14. Specifically, a puller wire 36 extends through the non-conductive cover 22 with a distal end anchored at or near the distal end of the inner member 14 and a proximal end anchored to the control handle 16, as described further below. The puller wire 36 is made of any suitable metal, such as stainless steel or Nitinol, and is preferably coated with Teflon® or the like to impart lubricity to the puller wire. The puller wire 36 preferably has a diameter ranging from about 0.006 to about 0.010 inches.

A preferred mechanism for anchoring the puller wire 36 to the inner member 14 comprises a T-bar anchor 39 anchored within the plastic cap 28 by glue or the like. If the inner member 14 includes multiple lumens, the T-bar anchor 39 can be anchored to the plastic cap 28 as generally described in U.S. Pat. Nos. 5,893,885 and 6,066,125, the entire disclosures of which are incorporated herein by reference. If the inner member 14 carries a tip electrode, the puller wire 36 can be anchored in the tip electrode, as also described in U.S. Pat. No. 6,066,125. Alternatively, the puller wire 36 can be anchored to the side of the inner member 14, as generally described in U.S. Pat. No. 6,123, 699, the entire disclosure of which is incorporated herein by reference. Other arrangements for anchoring a puller wire 36 to the distal end of the inner member 14 are included within the scope of the invention. If desired, a compression coil (not shown) may be provided in surrounding relation to the puller wire 36 within the catheter body 12, as described in U.S. Pat. No. 6,066,125.

Longitudinal movement of the stiffening member 20 to affect extension and retraction of the inner member 14 is accomplished by suitable manipulation of the control handle 16. Similarly, longitudinal movement of the puller wire 36 relative to the catheter body 12, which results in deflection of the inner member 14, is accomplished by suitable manipulation of the control handle 16.

Figure 4:
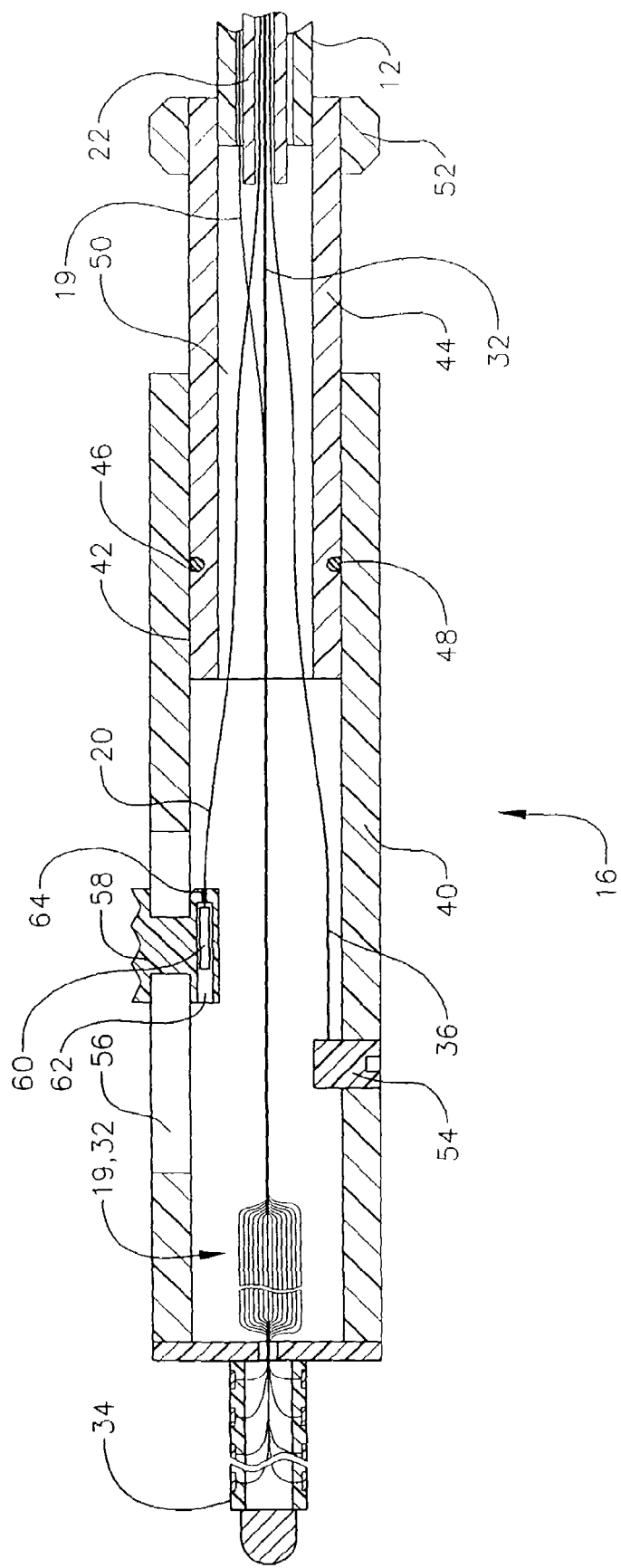
FIG. 4 is a side cross-sectional view of the control handle of the catheter of FIG. 1.

As shown in FIGS. 1 and 4, a preferred control handle comprises a generally cylindrical housing 40 having a piston chamber 42 at its distal end. A generally cylindrical piston 44 is disposed within and generally coaxial with the piston chamber 42. The piston 44 includes a circumferential O-ring notch 46 that carries an O-ring 48 to provide a snug, watertight fit between the piston and the wall of the piston chamber 42. The piston 44 has an axial bore 50 along its length. The diameter of the axial bore 50 is approximately the same as the outer diameter of the catheter body 12. The proximal end of the catheter body 12 extends into the axial bore 50 and is fixedly attached, for example, by glue, to the piston 44. The stiffening member 20, puller wire 36, and electrode lead wires 19 and 32 extend from the inner member 14 or catheter body 12, through the axial bore 50 of the piston 44 and into the control handle 16.

The distal end of the piston 44 extends beyond the distal end of the housing 40 so that it can be manually controlled by the user. An annular thumb control 52 is attached at or near the distal end of the piston 44 to facilitate lengthwise movement of the piston relative to the housing 40.

For longitudinal movement of the stiffening member 20, the housing includes a longitudinal slot 56 extending therethrough. A slider 58 is slidably mounted in the longitudinal slot 56, as best shown in FIG. 1. The proximal end of the stiffening member 20 is anchored to the portion of the slider 58 that is contained within the handle housing 40 by any suitable method. A suitable method for anchoring the stiffening member 20 to the slider 58 involves use of a short stainless steel tubing 60 or the like mounted on the proximal end of the stiffening member. The slider 58 includes an opening 62 for receiving the stainless steel tubing 60 and a channel 64 distal to the opening having a size that permits the stiffening member 20 to pass therethrough but that prevents the stainless steel tubing from passing therethrough. Other mechanisms for anchoring the stiffening member 20 to the slider 58 are within the scope of the invention.

For longitudinal movement of the puller wire 36, the puller wire is anchored to the housing 40 by any suitable method. In the depicted embodiment, the puller wire 36 is anchored to the housing by means of an anchor 54 that extends into a transverse hole in the housing proximal to the piston chamber 42. Such a design is described in more detail in U.S. Pat. No. 5,383,923, the entire disclosure of which is incorporated herein by reference. In use, the distal end of the inner member 14, once moved to an extended position, can be curved or bent by moving the piston 44 distally out of the piston chamber 42 by pushing outwardly on the thumb control 52.

The precise control handle mechanisms used for deflection of the puller wire 36 and for extension of the inner member 14 can be modified as desired. For example, the slider 58 could instead be used for manipulation of the puller wire 36, and the piston 42 can be used for manipulation of the stiffening member 20. Other control handles capable of manipulating a plurality of wires can also be used in connection with the invention. Examples of such handles are disclosed in U.S. Pat. No. 6,066,125 and U.S. patent application Ser. No. 09/710,210, entitled "Deflectable Catheter with Modifiable Handle," the disclosures of which are incorporated herein by reference.

If desired, a catheter body puller wire (not shown) can also be provided for deflection of the distal end of the catheter body 12. With such a design, the catheter puller wire is anchored at its distal end to the distal end of the catheter body, as generally described in U.S. Pat. No. 6,123,699, and is anchored at its proximal end to the control handle 16. To manipulate the catheter body puller wire, the control handle would contain an additional deflection mechanism, such as an additional slider (not shown) in a separate slot. If desired, the distal end of the catheter body 12 can comprise a piece of tubing (not shown) that is more flexible than the rest of the catheter body and that contains an off-axis lumen (not shown) into which the distal end of the catheter puller wire extends, as generally described in U.S. Pat. No. 6,123,699.

If desired, the inner member 14 and/or the distal end of the catheter body 12 can also include one or more location sensors (not shown), such as an electromagnetic location sensor, for conveying locational information about the electrodes on the inner member and/or catheter body. Use and design of such location sensors are described in more detail in U.S. application Ser. No. 10/040,932, entitled "Catheter Having Multiple Spines Each Having Electrical Mapping and Location Sensing Capabilities," the disclosure of which is incorporated herein by reference.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. Accordingly, the foregoing description should not be read as pertaining only to the precise structures described and shown in the accompanying drawings, but rather should be read as consistent with and as support for the following claims, which are to have their fullest and fairest scope.

What is claimed is:

1. A catheter comprising:

an elongated catheter body having a proximal end, a distal end and a lumen extending longitudinally therethrough;

a control handle attached to the proximal end of the catheter body, the control handle including first and second members that are moveable relative to each other, the second member being attached to the catheter body;

an inner member slidably mounted in the lumen of the catheter body, the inner member having proximal and distal ends and comprising an elongated stiffening member and a non-conductive cover surrounding the stiffening member, the inner member having a free distal end on which is mounted one or more electrodes, the catheter body comprising a non-conductive sleeve mounted in the lumen of the catheter body, wherein the inner member extends through the non-conductive sleeve;

wherein the proximal end of the inner member is attached to the first member of the control handle; and wherein longitudinal movement of the first member of the control handle relative to the second member of the control handle results in longitudinal movement of the inner member relative to the catheter body to cause the inner member to extend out of or retract into the catheter body.

2. The catheter of claim 1, further comprising means for deflecting the distal end of the inner member.

3. The catheter of claim 1, further comprising a puller wire extending through the catheter body and inner member, the puller wire having a distal end anchored at or near the distal end of the non-conductive cover and a proximal end anchored to a third member of the control handle, the third member being moveable relative to the second member so that movement of the third member relative to the second member results in longitudinal movement of the puller wire relative to the catheter body to thereby deflect the distal end of the inner member.

4. The catheter of claim 1, wherein an atraumatic tip is provided at the distal end of the non-conductive cover.

5. The catheter of claim 1, wherein a plastic cap is mounted at the distal end of the non-conductive cover.

6. The catheter of claim 1, wherein the inner member carries from about 2 to about 20 ring electrodes along its length.

7. The catheter of claim 1, wherein the inner member carries from about 3 to about 15 ring electrodes along its length.

8. The catheter of claim 1, further comprising one or more electrodes mounted at or near the distal end of the catheter body.

9. The catheter of claim 1, wherein the inner member further comprises at least one location sensor.

10. The catheter of claim 1, wherein the inner member is moveable between a retracted position, wherein the inner member is generally contained within the lumen of the catheter body, and an extended position, wherein the one or more electrodes on the inner member are generally positioned beyond the distal end of the catheter body.

11. The catheter of claim 10, wherein when the inner member is in the fully extended position, it has an exposed length ranging from about 10 mm to about 200 mm.

12. The catheter of claim 1, wherein the lumen is coaxial with the catheter body.

* * * * *